(12) United States Patent
Gandhi et al.

(10) Patent No.: US 7,298,475 B2
(45) Date of Patent: Nov. 20, 2007

(54) METHOD AND APPARATUS FOR STAND-OFF CHEMICAL DETECTION

(75) Inventors: Sunilkumar Babulal Gandhi, Salisbury (GB); Paul Douglas Jeffery, Salisbury (GB); Gerard David McAnally, Salisbury (GB)

(73) Assignee: The Secretary of State for Defence (GB)

( * ) Notice: Subject to any disclaimer, the term of this patent is extended or adjusted under 35 U.S.C. 154(b) by 258 days.

(21) Appl. No.: 10/524,467

(22) PCT Filed: Aug. 6, 2003

(86) PCT No.: PCT/GB03/03440

§ 371 (c)(1),
(2), (4) Date: Feb. 14, 2005

(87) PCT Pub. No.: WO2004/019020

PCT Pub. Date: Mar. 4, 2004

(65) Prior Publication Data

US 2006/0023211 A1 Feb. 2, 2006

(30) Foreign Application Priority Data

Aug. 22, 2002 (GB) ................... 0219541.0

(51) Int. Cl.
*G01J 3/30* (2006.01)
(52) U.S. Cl. .................. 356/318; 250/459.1
(58) Field of Classification Search ............. 356/318
See application file for complete search history.

(56) References Cited

U.S. PATENT DOCUMENTS

| | | | |
|---|---|---|---|
| 4,247,770 A | 1/1981 | Welch | |
| 4,393,311 A | 7/1983 | Feldman et al. | |
| 4,988,879 A | 1/1991 | Zare et al. | |
| 5,135,870 A | 8/1992 | Williams et al. | |
| 5,241,179 A | 8/1993 | Carrieri | |
| 5,443,793 A | 8/1995 | Ehrlich et al. | |
| 5,580,733 A | 12/1996 | Lewis et al. | |
| 5,757,484 A * | 5/1998 | Miles et al. | 356/318 |
| 5,847,825 A | 12/1998 | Alexander | |
| 5,946,089 A * | 8/1999 | Duer | 356/318 |
| 5,982,486 A | 11/1999 | Wang | |
| 6,008,897 A | 12/1999 | Sabsabi et al. | |
| 6,147,754 A * | 11/2000 | Theriault et al. | 356/318 |
| 6,771,368 B1 * | 8/2004 | Chadwick | 356/318 |

FOREIGN PATENT DOCUMENTS

| | | |
|---|---|---|
| GB | 2169496 | 7/1986 |
| WO | WO 01/93305 | 12/2001 |

OTHER PUBLICATIONS

Wikipedia, "Plasma (physics)", Dec. 15, 2006, Online, Internet, Wimimedia Foundation, Inc., http://en.wikipedia.org/wiki/Plasma_(physics)#Temperatures.*

* cited by examiner

*Primary Examiner*—Layla G. Lauchman
*Assistant Examiner*—Kara Geisel
(74) *Attorney, Agent, or Firm*—Dean W. Russell; Kilpatrick Stockton LLP

(57) ABSTRACT

A method, suitable for stand off analysis of a sample (2), comprising: (i) using an excitation means (6) to vaporise the sample (2) thereby producing a vapour plume (10) of molecular species; and (ii) using an analytical means (12) to analyse molecular species within the vapour plume (10) wherein the analytical means (12) analyses the molecular emission spectra of the vapour plume (10). The invention also relates to a kit and an apparatus for use with the same.

14 Claims, 1 Drawing Sheet

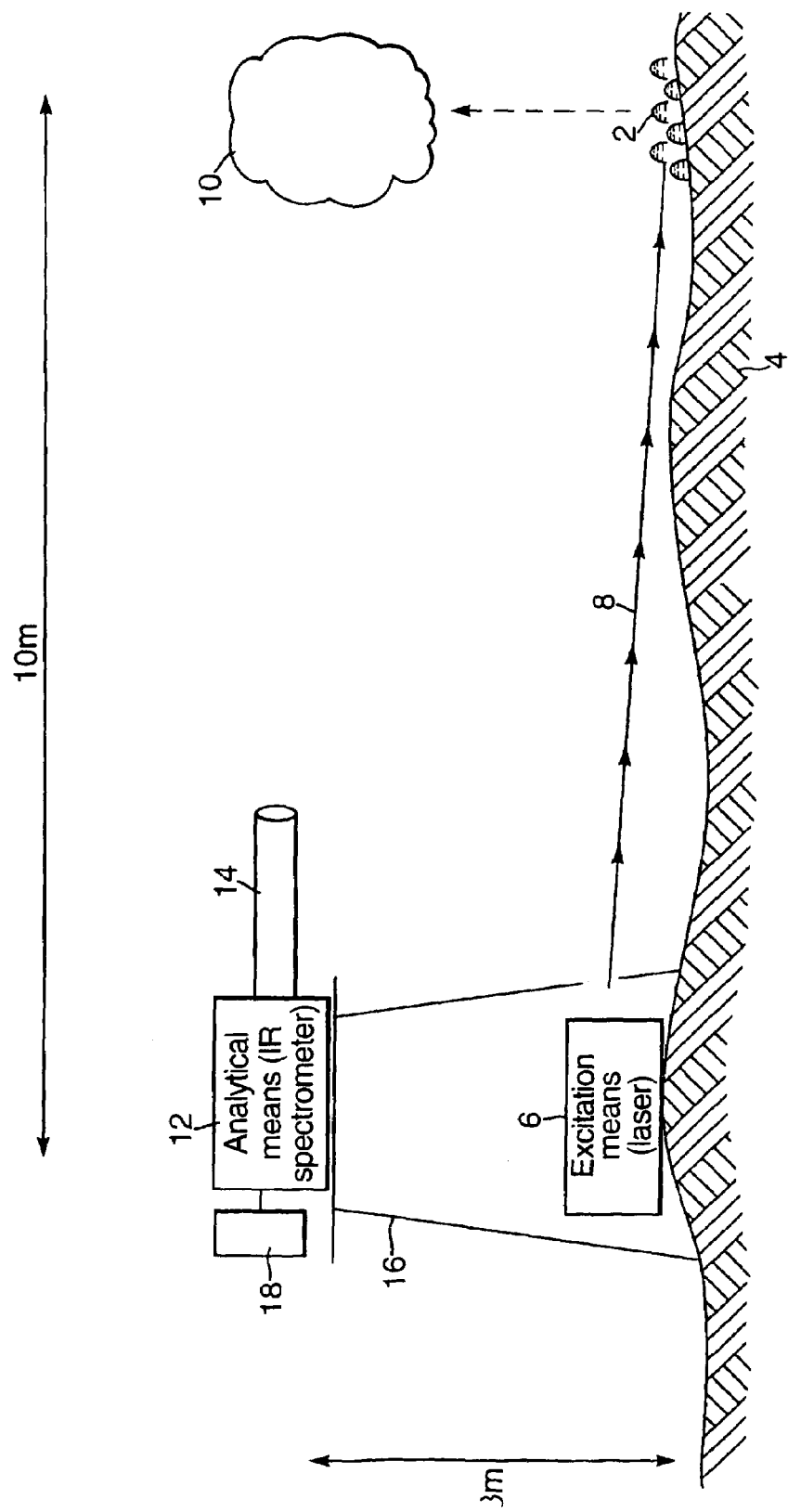

METHOD AND APPARATUS FOR STAND-OFF CHEMICAL DETECTION

CROSS REFERENCE TO RELATED APPLICATIONS

This application is the U.S. national phase of International Application No. PCT/GB2003/003440 filed on Aug. 6, 2003 and published in English on Mar. 4, 2004 as International Publication No. WO 2004/019020 A1, which application claims priority to Great Britain Application No. 0219541.0 filed on Aug. 22, 2002, the contents of which are incorporated by reference herein.

This invention relates to a method for detection and identification of one or more chemical species. More particularly this invention relates to a method for the stand-off vaporisation and identification of one or more materials with low volatility. This invention also relates to an apparatus and kit for implementing the method.

Many materials and substances are deposited on land or water for a variety of different reasons and if they are unwanted and/or dangerous they become contaminants, pollutants and toxic to the land or water. To effectively remediate the area it is important to accurately detect and identify such contaminants. Recently a new concern has arisen that during a time of conflict, or as an act of terrorism, unknown pollutants, including chemical and or biological warfare agents, may be deliberately used to contaminate and pollute land or water. It is particularly important that, prior to troops or civilians entering such an area, the contaminant is identified so that personnel are not subjected to unnecessary danger, appropriate protective clothing can be used, antidotes can be administered as necessary, and the land or water can be safely and successfully remediated.

Currently contamination is assessed by physically sampling the land or water and analysing the samples using either in the field analysis for example by mass spectrometry, or transmitting the sample to a laboratory. Although this can successfully identify a wide variety of contaminants including materials with low volatility, the methods are unsuitable for use in the field to identify unknown and potentially hazardous materials. This is because the sampling and analysis poses a real risk to the personnel involved and because the methods are too slow for effective use during conflict. To date the risk has been reduced by modifying the standard sampling and analysis in several ways including having personnel wear full protective clothing to sample the land or water, or by using for example detection papers to identify the contaminant. However, problems remain, including that without a detailed knowledge of the contaminant it can be difficult to assess the most appropriate clothing, during conflict it is impractical for front line troops to carry large amounts of protective gear and during collection the clothing itself is cross contaminated through exposure. Furthermore detection papers, although providing real time analysis of the material present, only give a crude assessment of the nature of the contaminant which may then require further analysis in a laboratory to enable full positive identification. In an attempt to overcome these problems a personnel operated vehicle has been developed for use on land comprising key sampling and analytical instrumentation. However, the use of such a vehicle still has several associated problems including contamination of the vehicle during use, exposure of the personnel operating the vehicle either when they enter the contaminated area or conduct the analysis, cost of the vehicle and transportation of the vehicle to the front line.

There remains a need to develop a totally stand-off method of contaminant detection and analysis whereby there is no requirement for personnel or equipment to come into contact with the sample yet which is able to quickly and accurately determine the nature of a wide variety of pollutants including those with low volatility. Such a method would reduce the risk of exposure to personnel and also remove the problem of equipment contamination. Furthermore such a method should ideally be capable of producing accurate results even in the situation where only low levels of pollutant are present, be transportable for use at the front line and should provide real time, or quasi real time, data to be used to direct a campaign.

Prior art has been identified relating to portable apparatus for the detection of a sample, including chemical and biological agents, comprising a laser and a mass spectrometer. Examples of such prior art include WO 01/93305, U.S. Pat. No. 5,580,733, U.S. Pat. No. 5,135,870 and U.S. Pat. No. 4,988,879. Although such disclosures provide an advance in sample detection several problems remain. These include that because such apparatus utilise a mass spectrometer, the sample and the detection means must be co-located and is therefore not suitable for stand off detection.

The review of the prior art has also highlighted that several methods are known for the remote and/or stand-off detection and analysis of gaseous materials. These include WO 92/09877 that describes an apparatus comprising a reflective element which transmits an infrared beam through a sample and returns it to a detector; WO 00/16070 that describes passing a composite beam of ultraviolet (UV) and infrared (IR) radiation through a sample and using a transfer module to direct the beam to a detector; U.S. Pat. No. 5,892,586 that describes passing many different radiations, each emitted from a micro-laser and tuned to a different absorption wavelength, through the sample and detecting the output; FR 2,349,831 that describes using a laser to produce uniform excitation and emission from a vapour which is then analysed; U.S. Pat. No. 5,294,796 that describes using a fixed wavelength laser to heat the background which then emits broadband infrared radiation back through the vapour from which the absorption is measured; and U.S. Pat. No. 4,490,613 which discloses directing a beam of high intensity IR radiation to energise the compounds in question and detect their re-radiation. Despite these developments several limitations remain. These include that some of the known methods are only useful for detection of gaseous materials; the methods often require tuning the instrumentation to a known wavelength to positively confirm the presence of a single component at once; many of the methods require complex optical and filtering means to deflect the radiation; and that some of the methods rely on heating of a background material which may not be practical in the field.

A further review of the prior art has indicated that methods have been developed for remote and/or stand-off surface analysis of a solid. These include U.S. Pat. No. 4,247,770 that describes directing a laser from an aircraft to an area of land, vaporising a sample and either analysing the atomic emission spectra or using a second laser to generate Raman and fluorescence spectra; U.S. Pat. No. 5,379,103 that describes using a fibre optic cable to deliver pulsed energy to a sample and using the emission spectra to identify the heavy metal or aromatic organic pollutants; U.S. Pat. No. 5,889,587, WO 93/97453, and U.S. Pat. No. 5,526,110 that all describe using an optical cable to direct a laser to a surface where the sample is ablated, carried to a plasma, dissociated and then analysed; U.S. Pat. No. 6,008,897 that describes a method and apparatus for laser-induced plasma spectroscopy of unknown heterogeneous materials; U.S. Pat. No. 4,191,475 that describes an apparatus which uses a laser to volatilise and excite a sample to the point of decomposition and then records the emission spectra; and U.S. Pat. No. 4,182,574 that describes laser spectral analysis of the atomic emission of chemical components in a target material. As previously, although the prior art discloses several improvements in surface analysis there remain several problems when these techniques are considered to solve the present problem. These include that some of the methods described rely on generating a plasma to interact with the material allowing for subsequent identification using atomic emission or fluorescence spectra which is insufficiently selective to accurately differentiate and identify between a wide range of different materials with low volatility, especially a wide range of organic materials; many of the methods disclosed are operated remotely but are not fully stand-off which results in continued personnel risk and equipment contamination; and, as previously, many of the methods require complex optical and filtering means which might not be practical to position in the field.

The prior art has also disclosed methods for identification of unknown chemical species, including liquids, by heating the material and detecting the energy re-emitted by the bulk. Examples of these disclosures include U.S. Pat. No. 4,496,839 and "Infrared detection of liquids on terrestrial surfaces by $CO_2$ laser heating" by Arthur H. Carrieri, Applied Optics 1990 Vol 29, No 33. However this method is slow because of the requirement to heat the substrate sufficiently to generate a thermal contrast, then acquire and process data and also difficult to use to identify when only a small amount of sample is present. Furthermore U.S. Pat. No. 5,241,179 discloses an apparatus for remotely detecting liquid contaminants on surfaces comprising a an infrared spectrometer aligned to detect the photoluminescence spectra irradiated from the contaminant generated when a laser is used to irradiate the surface upon which the contaminant resides. Again while such an apparatus presents an advance in the field problems still exits. These include that irradiating the substrate may only provide a weak absorption signal from the contaminant if insufficient energy is transferred from the substrate to the contaminant, heating the substrate sufficiently may require an unduly large amount of energy, and that the contaminant may produce both absorption and emission spectra which lead to a false negative result.

There remains a need to develop an improved method, and associated apparatus, that enables quick and accurate stand-off analysis and positive quasi real time in the field identification of solids and liquids, particularly those with low volatility. In order to be able to be used in a stand-off manner it is important that the method does not operate at wavelengths that would be masked by the absorption bands of the atmosphere itself The method should be flexible enough to be used with a wide variety of different materials, should be able to identify individual compounds when presented with a mixture of compounds, and should have sufficient selectivity to be able to differentiate between closely related compounds. Such a method should be sensitive enough to be useable even when only a very small amount of the material is present or the material is present at a low concentration. The problem also remains as to how to achieve this technical result with equipment which is easy to transport to the front line during a military campaign, can be operated by personnel with little or no specific scientific training, can be used to equal effect in a wide variety of different in-field situations, including for identification of land or water contamination, and does not require the arrangement of complex optical or filtering means around the sample, or access to the sample from specific angles, for effective operation.

A method and associated apparatus has now been developed which allows for stand-off interrogation and accurate analysis of a wide range of materials including solids and liquids with low volatility. Without wishing to be bound by theory the method comprises a first step in which an excitation means, preferably a laser operating at a single wavelength which is not necessarily related to the absorption characteristics of the sample, is used to volatilise the sample to produce a vapour plume of molecular species which are excited. In a second step a stand-off analytical means, for example an infrared spectrometer preferably fitted with a means for collecting light from the sample, is used to analyse the molecular emission spectra of the vapour plume. In order to achieve the desired level of analytical selectivity this method has been designed to analyse the molecular spectral characteristics, including vibrational characteristics, of the sample. This method has also been designed such that the analytical step does not rely on the use of a second energy source to further excite the sample to create secondary emission or fluorescence thereby reducing the complexity of the method. This method and associated apparatus have several advantages over the prior art including that they provide an accurate means for remotely interrogating and analysing a wide variety of materials including solids and liquids with low volatility across a broad wavelength spectrum, and which relies only on a single excitation means and whereby the excitation means can be a single wavelength non-specific laser. The method is sensitive enough to be used when only low levels of the sample are present, can identify components when presented with a mixture of materials, and is also sufficiently selective to differentiate between closely related materials in real time or quasi real time. Furthermore the method is flexible such that there is no special need for the laser and the analytical instrument to have a specific orientation with respect to either each other or the sample, nor is there a requirement for the use of additional lenses or filters to achieve the spectroscopic effect. This means that the instrumentation associated with the method can be designed to be small and portable for use at the front line and can be used even when it is not possible to have access to the sample from all possible angles. Finally the instrumentation is relatively simple ensuring that it can be readily used by personnel with little or no specific scientific training.

It is an object of the present invention to develop a method and associated apparatus capable of stand-off interrogation and analysis of a wide variety of materials including liquids and solids with low volatility. It is another object of this invention to develop such a method to be sensitive enough to be useable when only low level of samples are present, to have the capability to identify components of a mixture, and is selective enough to differentiate between closely related materials. It is a further object of this invention to develop such a method that is able to provide real time or quasi real time analysis. It is also an object of this invention to develop an apparatus that is portable so that it can be readily used in a variety of different situations, including at the front line during a campaign, and that it can be readily operated by non-scientifically trained personnel. These, and other objects of this invention, will become apparent in light of the following disclosure.

SUMMARY OF THE INVENTION

According to a first aspect this invention relates to a method, suitable for stand off analysis of a sample, comprising:

(i) using an excitation means to vaporise the sample thereby producing a vapour plume of molecular species; and (ii) using an analytical means to analyse the molecular species within the vapour plume wherein the analytical means analyses the molecular emission spectra of the vapour plume.

According to a second aspect, this invention relates to a kit suitable for stand off analysis of a sample, comprising:

(i) an excitation means; and (ii) an analytical means, whereby the excitation means is arranged such that it can be used to vaporise the sample thereby producing a vapour plume of molecular species and whereby the analytical means is arranged to analyse the emission spectra of the molecular species within the vapour plume.

According to a third aspect, this invention relates to an apparatus suitable for stand off analysis of a sample, comprising:

(i) an excitation means; and (ii) an analytical means;

whereby the excitation means is arranged such that it can be used to vaporise the sample thereby producing a vapour plume of molecular species and whereby the analytical means is arranged to analyse the emission spectra of the molecular species within the vapour plume.

DETAILED DESCRIPTION OF THE INVENTION

All publications cited herein are hereby incorporated by reference in their entirety, unless otherwise indicated.

The elements of the apparatus are described in more detail below.

As used herein the term remote shall be taken to mean that an operator of an instrument is not co-located with a sample but that some feature of the instrumentation is co-located with the sample.

As used herein the term stand-off shall be taken to mean that neither an operator nor any element of instrumentation is co-located with a sample. As such when an apparatus is stand-off there is no risk of sample contamination to either personnel or equipment.

As used herein the term vaporise shall be taken to mean that at least some of the sample has been converted to a vapour.

As used herein the term low volatility shall be taken to mean that, at atmospheric temperature and pressure, only an intangible level, if any, of the sample exists in the gaseous and/or vapour phase and as such the sample has, at atmospheric temperature and pressure, a vapour pressure of less than water.

As used herein the term molecular species shall be taken to mean a species that comprises one or more atoms linked by chemical bonds and whereby at least one of these bonds is consistent with at least one of the bonds present in the parent sample.

The molecular species may be neutral or charged.

As used herein the term plume shall be taken to mean a cloud of vapour. There will be many different types of molecular species that will be present in the plume and these will likely comprise a mixture of one or more of the vaporised parent sample materials, fragment species obtained by dissociation of one or more of the chemical bonds in the parent sample, or ionised species of the parent material or fragments.

The present invention relates to a method, suitable for stand off analysis of a sample, comprising:

(i) using an excitation means to vaporise the sample thereby producing a vapour plume of molecular species; and (ii) using an analytical means to analyse the molecular species within the vapour plume wherein the analytical means analyses the molecular emission spectra of the vapour plume.

The method is a stand-off method enabling the positive identification of a sample material. It has been designed to be flexible such that it can be used in a wide variety of different locations. The sample is contained on a substrate within a target area. Suitable substrates include land and water, preferably land. Examples of land substrates include sand, concrete, tarmac, asphalt, soil, grass and the like. Since the method relies on the production of a vapour plume from the sample material it cannot in general be used in an environment where there is not a gaseous atmosphere for example underwater, but with the exception that it could be conducted in a vacuum or partial vacuum if required.

The method of the present invention has been designed such that it can be used for a wide variety of samples, but it is particularly effective for the identification of samples that have a low volatility at atmospheric temperature and pressure. The sample to be analysed is optionally a solid or a liquid, preferably a liquid and more preferably an organic liquid. It is preferred that, at 20° C. and 1 Atm pressure, the sample has a vapour pressure of less than about 0.02 Atm, preferably less than about 0.001 Atm, and more preferably less than about 0.001 Atm. Furthermore the method has been designed such that, if a sample comprises more than one different component, it can positively identify individual components. As such the sample to be analysed may comprise a mixture of one or more of a solid material, a mixture of one or more of a liquid material or a mixture of one or more of a solid material in conjunction with one or more of a liquid material. The sample may optionally comprise one or more carrier materials or thickening agents. In addition the sample may be a solution, suspension, or a colloid or other type of mixture. Furthermore the method has been designed such that it is selective enough to be able to positively differentiate between different components within a sample including to identify carrier components, and it may also differentiate between different components which are closely related or of a similar nature.

In order that the method is able to work effectively it must be possible to vaporise at least a small amount of the sample from the surface of the substrate. As such the sample to be vaporised should preferably be present on the surface of the substrate but the method may also be used if the material has been absorbed only a short distance into the substrate or if the sample is present in solution within the substrate. In order to allow for such circumstances, the method of the present invention is sensitive enough that it can be usefully used to analyse material when even only a very low level of pollutant is present. For example the method of the present invention is able to positively identify a material when presented with as little as a droplet or grain with a diameter of as small as 0.1 mm, or more likely as small as 1 mm. There is no maximum restriction on the size of the contaminant that can be successfully analysed with this method. In addition, when the sample is a solution or mixture of one or more materials in a solvent or other carrier material, the method is sensitive to be able to identify the relevant components when the material is present at only very low concentrations, for example if the material is present at a concentration of about 1 mM, or even 1 µM.

The method of the present invention uses an excitation means to vaporise the sample. In order for the method of the present invention to have sufficient sensitivity and selectivity it is necessary that the excitation means only uses sufficient excitation power to vaporise the sample to produce a vapour plume wherein at least some of the molecular integrity of the sample itself has been maintained. As such the vapour plume should comprise at least one molecular species comprising at least one of the chemical bonds present in at least one of the components of the parent sample. The excitation step may interact with the one or more components of the sample material to cause dissociation or ionisation. However, in order to obtain good spectral data, it is preferred that, for each component present in the sample, the plume comprises at least some of the component in a non-dissociated and non-ionised state. In addition it is preferred that the excitation means does not result in the ionisation of the atmosphere or the substrate and it is preferred that the excitation step does not result in the formation of a plasma. As such, samples which have a extremely low volatility, for example metals, are unlikely to be readily analysed using this method since it would be very difficult to identify an excitation means which is able to produce a vapour plume from the sample without dissociating the sample completely and/or producing a plasma. The excitation means should excite the molecular species within the vapour plume sufficiently so that the vapour plume is hotter than the surrounding atmosphere by at least about 0.1K, preferably by about 1K, and more preferably by about 5K. When the vapour plume is sufficiently excited it is described as a hot vapour plume.

Once sufficient sample has been volatilised then the excitation means can be turned off which saves power. This method does not require that the background is heated, or that a bulk sample is heated, or that a plasma is produced. This further reduces the level of energy required from the excitation means making the method ideal for use in the field where power requirements may be at a premium. The actual level of energy required by the excitation means will vary depending on several factors including the likely nature of the contaminant, the nature of the excitation means, the distance of the excitation means from the sample and also the atmosphere in which the method will be operated. The level of energy for any particular scenario can be readily determined by one skilled in the art.

In the method of the present invention the excitation means is directed towards the sample material on a suitable substrate. In the field this will usually be the ground or water. Provided that sufficient energy from the excitation means reaches the sample to enable it to be vaporised, then there is no requirement that the excitation means be able to be accurately focussed on the sample. This has the advantage that the excitation means can be used to vaporise a sample from a long distance or in the instance where the exact location of even a low level of contaminant may not be precisely known. However, the more accurately the excitation means can be focussed on the sample within the target area, the less the power that will be required to vaporise the sample. As such it is preferred that the excitation means can be accurately focussed such that it can be targeted directly to the sample where possible. To enable the excitation means to be more accurately directed towards a sample on a substrate, it is possible to raise the excitation means onto a platform. The height of such a platform may vary considerably from instance to instance but can be determined by one skilled in the art determining the distance of the sample, the focal length of the excitation means, the angle to the sample, the curvature of the earth and the like. However for practical reasons it is preferred that the height of the platform is not higher than about 10 m, preferably not higher than about 5 m.

In order that the method of the present invention is able to usefully be used in a stand off mode for the analysis of a sample it is preferred that the excitation means can effectively vaporise at least some of the sample at a distance of greater than about 10 m, preferably greater than about 30 m, more preferably greater than about 50 m and most preferably greater than about 100 m from the sample. At such distances it may be necessary to raise the excitation means to a height of from about 1 m to about 20 m, preferably less than about 10 m, more preferably less than about 5 m and most preferably about 3 m above the substrate to be able to direct the excitation means towards the sample as accurately as possible. The exact height required will depend on the distance of the sample and the focussing angle from the instrument to the sample. Any suitable means can be used to raise the means for example a tower or platform. However, since it is envisaged that this equipment would be used in the field by ground forces or personnel, it is unlikely that the range of the excitation means would be required to be greater than 1000 m. When used at long distances it may be necessary for one skilled in the art to adjust the excitation means accordingly to achieve the desired sample vaporisation. In performing such an adjustment it is necessary to consider whether or not the wavelength of the excitation means is on or off resonance with an absorption band of the sample itself, the manner in which the energy is delivered and the required focussing of the excitation means. By adjusting each of these with respect to each other, an excitation means can be achieved whereby the sample is heated most efficiently to produce a vapour plume.

The preferred excitation means for use with the method of the present invention is a laser because the power of the laser can be controlled and the laser beam can be focussed to target a specific area. This latter feature means that lasers are ideally suited for use when only a low level of sample is present and means that the instrument can be used flexibly in instances where the sample is at different distances from the user. Lasers for use with the present invention can operate at any wavelength provided they can deliver sufficient power to vaporise at least some of the sample. They can be operated as tuneable wavelength lasers or fixed wavelength lasers. In order for this method to operate effectively there is no requirement that the laser beam be tuneable to any specific wavelength related to the absorption bands of the sample in question. Thus, in order to reduce complexity and minimise costs, it is preferred that the laser is operated at a fixed wavelength. Since the method does not rely on collecting data at a specific wavelength, the chosen fixed wavelength of the laser need not necessarily be related to any given absorption wavelength of any species in the sample. Again provided that the laser delivers sufficient power, the laser can be operated as a pulsed laser or as a continuous wave laser. It is preferred that the laser is a continuous wave laser since this is more likely to provide a continuous stream of vapour for analysis. It is further possible that if the laser is a continuous wave laser that it be a modulated continuous wave laser. This is preferred since it can be used in combination with appropriate detection means capable of demodulating or otherwise processing the signal to achieve a higher level of detection sensitivity and can also result in the avoidance of non modulated signals which may otherwise interfere with the results.

Suitable powers for a continuous wave laser are greater than about 2 watts, more preferably greater than about 5 watts, and even more preferably greater than about 10 watts or equivalent. However it is important that the power of the laser is not so large as to, within the plume, dissociate all of the molecular species to form atoms or ions as a plasma or otherwise. This is because such plasma would be of insufficient selectivity for use in the present invention. As such it is preferred that a continuous wave laser has a power of less than about 150 watts, more preferably less than about 50 watts and even more preferably less than about 20 watts. If the excitation means is a laser, but is not a continuous wave laser, for example if it is a pulsed laser, then a power equivalence to the above should be used and these can be determined readily by one skilled in the art according to the system in question. For a pulsed laser the power level should be selected such that mean power delivered to the sample is equivalent to that of a continuous wave laser.

A wide variety of different lasers can be used in the method of the present invention including Neodymium Yttrium Aluminium Garnet laser; Titanium sapphire laser; carbon dioxide laser. The preferred laser type is a carbon dioxide laser. Alternatively the laser could optionally be based around an optical parametric oscillator, such as those known in the art, specifically configured to provide tuneable infrared radiation.

The method of the present invention uses an analytical means to analyse the molecular species within the vapour plume wherein the analytical means is capable of analysing the molecular emission spectra of the vapour plume. Any suitable analytical means may be used. To minimise the complexity of the equipment it is preferred that the analytical means is able to analyse the vapour plume without an additional need for secondary excitation of the vapour plume. Furthermore it is also preferred that, in order to obtain the necessary analytical signals from the sample, there is no requirement for the background to be excited to provide a radiation emission source. One advantage of this simplicity is that the method of the present invention need only comprise the use of a single excitation means. Utilising an analytical means that is capable of analysing the molecular emission spectra of the vapour plume is one means by which the secondary excitation of the sample may be avoided.

One example of a suitable technique is infrared spectroscopy. In order to be able to use infrared spectroscopy to analyse the emission spectra of the molecular species in the vapour plume it is necessary that the temperature of the vapour plume is hotter than the surrounding atmosphere by at least about 0.1K, preferably by about 1K, and more preferably by about 5K. A further advantage of infrared spectroscopy is that it is a technique with the inherent sensitivity and selectivity properties that make it ideal for allowing for the accurate identification of, and differentiation between, a wide variety of different materials and also it can be used in atmospheric conditions without fear of any emission spectra from the background interfering with the spectral data of the sample in question. In addition, by comparing the results with known libraries of data it is possible for infrared spectroscopy to be used to identify individual components in a mixture of materials. In accordance with above, it is preferred that the analytical means is an infrared spectrometer. In order to enhance the analytical capability of the infrared spectrometer it is preferred that the spectrometer is a rapid scanning infrared spectrometer and more preferably a rapid scanning Fourier transform infrared spectrometer or other measurement and processing technique for example image multi-spectra sensing as disclosed in U.S. Pat. No. 5,479,258.

It is preferred that the analytical means is linked to a computer which is able to employ software to process the analytical data and provide a meaningful result for the user. The computer preferably has a memory having a library of analytical data that have been developed under controlled conditions for likely known contaminants at known concentrations. The computer compares the data obtained to the known data in its library. It is preferred that either a peak identification technique or other quantitative data analysis technique is employed. By this analysis the identity of the contaminant material in the target area can be determined. The computer preferably operates continuously such that the analysis of the vapour sample can proceed simultaneously or nearly simultaneously thereby providing real-time or near real-time monitoring.

In order that the method of the present invention may be used in a stand-off manner it is preferred that the analytical means is fitted with a means for stand-off detection of the analytical signals from the vapour plume. One important feature that leads to the success of this method is the ability to analyse the sample material in a stand-off manner without there being any necessity that the sample and the analytical instrumentation are co-located. Example of such means may include one or more of an emission port, one or more lenses or a reflective telescope. It is preferred that the means for the stand-off detection of analytical signals from the vapour plume is an reflective telescope. Examples of reflective telescopes include a Newtonian telescope or a Cassegrain telescope. It is preferred to use a Cassegrain telescope. In order to simplify the operation of the equipment and reduce the risk to personnel it is preferred that the means for stand-off detection of the analytical signals from the vapour plume is able to operate effectively over a distance similar to that over which the excitation means is able to vaporise the sample. If a reflective telescope is being used it is preferred that the field of view of the telescope can be varied such that the instrument can be used flexibly when the sample is at different distances. It is preferred to use an infinity focussed reflective telescope.

Examples of infrared spectrometers which have been fitted with a means for stand-off detection of the analytical signals include OPAG 22 supplied by Bruker Optik GmbH (Rudolf-Plank-Str. 23, 76275 Ettlingen, Germany); MIDAC AM supplied by MIDAC Corporation (17911 Fitch Avenue, Irvine, Calif., USA); MR Series IR Spectrometers supplied by AB Bomem Inc (585 Charest Boulevard East, suite 300, Quebec, Canada); and the Model 500 Fourier Transform Infrared spectrometer supplied by Block Engineering (72 Cedar Hill Street, Marlborough, Mass., USA).

In order that the analytical means is able to operate effectively it is important to produce sufficient vapour plume that the means for stand-off detection of the analytical signals is able to identify the sample. This requirement will vary considerably from instrument to instrument and will need to be identified by one skilled in the art on a case by case basis. The excitation means will need to be adjusted to ensure that sufficient vapour is produced. In some instruments it may be possible to adjust the field of view of the detection means such that the plume adequately fills the field of view. Optionally the instrument may be fitted with a sight to help to ensure that it is aligned correctly. Optionally the instrument may be fitted with a filter to remove any scattered or reflected laser radiation from the field of view of the analytical means such that the spectral results are not distorted. It is preferred that sufficient vapour plume is produced to at least partially, and preferably fully, fill the field of view of the analytical means. As with the excitation means, it may be helpful to place the analytical means onto a platform in order to enable it to be better directed towards the vapour plume. Here the height of the platform required will be dependent on the distance of the sample, the height of the hot vapour plume above the surface and the angle of the instrument to view the hot vapour plume.

In order to operate the method of the present invention the excitation means must be orientated such that it can be used to vaporise the sample to produce a vapour plume. Similarly the analytical means must be orientated such that the means for stand-off detection of the analytical signals is able to detect the vapour plume. Beyond this there is no specific requirement regarding the relative orientation of the laser with the analytical instrument. The two means should be orientated such that the operation of one does not interfere with the operation of the other. Preferably the means can be located side by side. Even more preferably the means are integrated into a single apparatus which is capable of performing both the first and second step of the present invention. The method of the present invention may optionally comprise further suitable optics that can be used, if necessary, to enable the accurate focusing of the excitation means onto the sample or to deflect the emitted radiation to the analytical means. It is preferred however that the method does not require such a means since this adds complexity to the system but, in the instance where it is not possible for logistical reasons to co-locate the excitation means with the analytical means, it may provide a useful manner by which to aid alignment of the different means required.

This invention also relates to a kit suitable for stand off analysis of a sample, comprising:
(i) an excitation means; and
(ii) an analytical means, whereby the excitation means is arranged such that it can be used to vaporise the sample thereby producing a vapour plume of molecular species and whereby the analytical means is arranged to analyse the emission spectra of the molecular species within the vapour plume.

Furthermore, this invention relates to an apparatus suitable for stand off analysis of a sample, comprising:
(i) an excitation means; and
(ii) an analytical means;

whereby the excitation means is arranged such that it can be used to vaporise the sample thereby producing a vapour plume of molecular species and whereby the analytical means is arranged to analyse the emission spectra of the molecular species within the vapour plume.

In designing a kit or apparatus for use with the method of the present invention, and for use in the field, it is important to bear in mind the following: making the apparatus as simple to use as possible such that it can be operated by personnel with little or no scientific training; minimising the size and weight of the equipment such that it can be easily transported; maximising the durability of the equipment for different situations, including different temperatures, and minimising the power requirement of the apparatus.

FIGURES

This invention will now be described by reference to the following drawings in which FIG. 1 shows operation of a method according to the present invention.

FIG. 1 shows several small droplets of liquid sample 2 resting on the surface of the ground 4. A laser excitation means 6 is situated on the ground 4 approximately 10 m away from the liquid sample 2. A radiation beam 8 is emitted from the laser 6 and focussed on the liquid sample 2. This vaporises the sample 2 to produce a vapour plume 10 directly above the liquid sample 2. An infrared spectrometer analytical means 12 is located alongside the laser excitation means 6 also approximately 10 m away from the liquid sample 2. The infrared spectrometer 12 is fitted with a telescope lens 14 that is focussed at infinity and directed towards the vapour plume 10. In order to aid direction of the spectrometer 12 towards the vapour plume 10, the infrared spectrometer 12 is situated on a platform 16 approximately 3 m above the ground. The telescope lens 14 and the infrared spectrometer 12 together are able to record emission data from the vapour plume 12. These data are then processed by the processing unit 18 to produce a spectra. The processing unit 18 is then able to compare the spectra to a known library to positively identify the one or more components in the liquid sample.

EXAMPLES

The following examples further illustrate the preferred embodiments within the scope of the present invention. These examples are given solely for the purpose of illustration and are not to be construed as limitations of the present invention as many variations of the invention are possible without departing from its spirit or scope.

Example 1

A continuous wave $CO_2$ laser (Edinburgh Instruments), operating at 9.6 µm, with an output power of 4.5 W, was situated approximately 1 m away from a droplet of liquid methyl salicylate of approximate diameter 10 mm. The laser beam was directed using appropriate mirrors and focussed on to the droplet using a lens made of zinc selenide and then used to vaporise the sample to create a vapour plume directly above the droplet. The infrared emission spectrum of the vapour plume was then measured using a MEDAC AM Fourier Transform Infrared (FTIR) spectrometer, with 1 m focal length collection lens placed in front of the open emission port, situated 1 m away from the vapour and positioned at right angles to the laser. The infrared spectrum was obtained by operating the FTIR at between 1 and 20 scans per second and using a suitable resolution of 1 to 32 $cm^{-1}$. The collected spectra were compared with library spectra to provide positive identification of the liquid methyl salicylate from its vapour. Successful analytical results have also been achieved by modifying the system to use a 2 m focal length lens or a 3 m focal length lens and moving the FTIR spectrometer to a distance of 2 m or 3 m from the plume respectively.

Example 2

A continuous wave $CO_2$ laser (Edinburgh Instruments), operating at 9.25 µm, with an output power of 10 W, was situated approximately 5 m away from a droplet of liquid chemical warfare agent of approximate diameter 10 mm. The laser beam was directed unfocussed on to the droplet and then used to vaporise the sample to create a vapour plume directly above the droplet. The infrared emission spectrum of the vapour plume was then measured using a MIDAC AM Fourier Transform Infrared (FTIR) spectrometer, fitted with a Cassegrain telescope with a diameter of 25 cm focused to infinity, situated 5 m away from the vapour and positioned alongside the laser. The infrared spectrum was obtained by operating the FTIR at between 1 and 20 scans per second and using a suitable resolution of 1 to 32 $cm^{-1}$. The collected spectra were compared with library spectra to provide positive identification of the individual components of the liquid chemical warfare agent mixture.

The invention claimed is:

1. A method, suitable for stand off analysis of a sample comprising one or more chemical and/or biological warfare agents of low volatility, said method comprising:
   (i) using an excitation means to vaporise the sample thereby producing a vapour plume of molecular species; and
   (ii) using an analytical means to analyse the molecular species within the vapour plume wherein the analytical means analyses the molecular emission spectra of the vapour plume and is provided with means to enable it to receive said spectra for stand off analysis.

2. A method according to claim 1 wherein the excitation means is a laser.

3. A method according to claim 2 wherein the laser is operated at a fixed wavelength.

4. A method according to claim 2 wherein the laser has a power of greater than 2 W.

5. A method according to claim 2 wherein the laser has a power of less than 150 W.

6. A method according to claim 2 wherein the laser is operated as continuous laser beam.

7. A method according to claim 2 wherein the laser is a carbon dioxide laser.

8. A method according to claim 1 wherein the method comprises the use of only a single excitation means.

9. A method according to claim 1 wherein the vapour plume is hotter than the surrounding atmosphere by at least 0.1K.

10. A method according to claim 9 wherein the vapour plume is hotter than the surrounding atmosphere by 1K.

11. A method according to claim 10 wherein the vapour plume is hotter than the surrounding atmosphere by 5K.

12. A method according to claim 9 wherein the analytical means is an infrared spectrometer.

13. A kit suitable for stand off analysis of a sample comprising one or more chemical and/or biological warfare agents of low volatility, said kit comprising:
   (i) an excitation means arranged such that it can be used to vaporise the sample thereby producing a vapour plume of molecular species;
   (ii) an analytical means arranged to analyse the emission spectra of the molecular species within the vapor plume; and
   (iii) means associated with the analytical means to enable said analytical means to receive the emission spectra from the vapour plume.

14. An apparatus suitable for stand off analysis of a sample comprising one or more chemical and/or biological warfare agents of low volatility, said apparatus comprising:
   (i) an excitation means arranged such that it can be used to vaporise the sample thereby producing a vapour plume of molecular species;
   (ii) an analytical means arranged to analyse the emission spectra of the molecular species within the vapour plume; and
   (iii) means associated with the analytical means to enable said analytical means to receive the emission spectra from the vapour plume.

* * * * *